(12) United States Patent
Pouteau et al.

(10) Patent No.: US 7,863,036 B2
(45) Date of Patent: Jan. 4, 2011

(54) BIOCHIP WITH INDEPENDENT RECOGNITION AREAS AND OPTICAL FORMAT AND FLOAT SCANNING THEREOF

(75) Inventors: Patrick Pouteau, Meylan (FR); Daniel Bec, Villeneuve-Tolosane (FR); Stephane Le Brun, Carbonne (FR)

(73) Assignees: Commissariat a l'Energie Atomique, Paris (FR); Biomerieux S.A., Marcy l'Etoile (FR)

( * ) Notice: Subject to any disclaimer, the term of this patent is extended or adjusted under 35 U.S.C. 154(b) by 1068 days.

(21) Appl. No.: 10/552,898

(22) PCT Filed: Apr. 21, 2004

(86) PCT No.: PCT/FR2004/050162

§ 371 (c)(1),
(2), (4) Date: Oct. 11, 2005

(87) PCT Pub. No.: WO2004/097380

PCT Pub. Date: Nov. 11, 2004

(65) Prior Publication Data

US 2006/0194205 A1    Aug. 31, 2006

(30) Foreign Application Priority Data

Apr. 23, 2003 (FR) .................................. 03 50124

(51) Int. Cl.
*C12M 1/34* (2006.01)
*C12M 3/00* (2006.01)

(52) U.S. Cl. .................................................. 435/287.2
(58) Field of Classification Search ................ 435/287.2
See application file for complete search history.

(56) References Cited

U.S. PATENT DOCUMENTS

| 5,083,035 | A | 1/1992 | Pecen et al. |
| 5,721,435 | A | 2/1998 | Troll |
| 6,090,555 | A | 7/2000 | Fiekowsky et al. |
| 6,537,801 | B1 * | 3/2003 | Ida et al. .................. 435/287.2 |
| 6,611,767 | B1 | 8/2003 | Fiekowsky et al. |
| 7,153,366 | B1 * | 12/2006 | Chen et al. .................. 118/620 |

(Continued)

FOREIGN PATENT DOCUMENTS

JP      2000-69998      3/2000

(Continued)

OTHER PUBLICATIONS

A. Kuklin: "High throughput screening of gene expression signatures", Genetica, vol. 108, pp. 41-46, 2000. XP-001095704.

*Primary Examiner*—Walter D Griffin
*Assistant Examiner*—Lydia Edwards
(74) *Attorney, Agent, or Firm*—Oblon, Spivak, McClelland, Maier & Neustadt, L.L.P.

(57) ABSTRACT

A biochip, and a device for reading the biochip, the biochip including a plurality of molecular recognition areas distributed with a determined layout to create a format of molecular recognition areas and a mechanism for making optical position marks for each molecular recognition area, distributed with a determined layout to form an optical format. The optical format and the format of recognition areas are formats produced independently of each other. A mechanism is provided determining the relative position of the two formats being provided on the biochip.

16 Claims, 4 Drawing Sheets

U.S. PATENT DOCUMENTS

| | | | | |
|---|---|---|---|---|
| 7,198,939 | B2 * | 4/2007 | Dorsel et al. | 435/283.1 |
| 2001/0044058 | A1 * | 11/2001 | Sogawa | 430/22 |
| 2002/0167751 | A1 * | 11/2002 | Lee et al. | 360/72.1 |

FOREIGN PATENT DOCUMENTS

| | | |
|---|---|---|
| JP | 2002-55050 | 2/2002 |
| JP | 2002-214232 | 7/2002 |
| JP | 2002-526773 | 8/2002 |
| JP | 2002-530786 | 9/2002 |
| JP | 2008-309801 | 12/2008 |
| WO | 98/01533 | 1/1998 |
| WO | 01/06395 | 1/2001 |

* cited by examiner

BIOCHIP WITH INDEPENDENT RECOGNITION AREAS AND OPTICAL FORMAT AND FLOAT SCANNING THEREOF

TECHNICAL FIELD

This invention relates to a biochip comprising a plurality of molecular recognition areas and optical marks to determine which molecular recognition areas will be actually read.

The invention also relates to reading of such a biochip and particularly its reading device.

STATE OF THE ART

Document FR-A-2 784 189. (corresponding to U.S. Pat. No. 6,537,801) divulges a biochip comprising a plurality of molecular recognition areas and a device for reading such a biochip. In particular, it describes a first mechanical system for the use of an optical read head to scan a biochip with optical marks and slaving of the precise position of the optical head using this first mechanical system or a second more specialised mechanical system. This slaving of the position of the optical head with respect to optical marks is more commonly referred to as tracking for Compact Disks (CDs). Precise reading of fluorescence is possible due to this slaving system controlling the precise position of the optical head. Optical marking patterns placed on the biochip may be in the form of tracks.

The optical format composed of marking patterns that gives information about the position of the fluorescence read performed. The format enables continuous repositioning of the optical head on its ideal trajectory. Due to the optical format, it is possible to know if the recorded fluorescence information originates from a specific recognition area. Therefore, this requires specific patterns, for example to indicate passage from one recognition area to another. This also requires at least partial numbering of read tracks or absolute control of track skips when the biochip is being scanned. The fluorescence information can thus be recorded directly and correlated to a specific recognition area positioned on the biochip.

Document FR-A-2 784 189 divulges important progress with respect to previously used techniques. However, any fault in the relative positioning on the biochip between recognition areas and patterns forming the optical format is a source of error. For example, a positioning error on all recognition areas may show up an offset such that one track in the optical format is located on the boundary between two adjacent recognition areas. This type of defect creates a problem because it can cause read errors by assigning a fluorescence measurement to one or the other of the adjacent biological probes. Thus, there is a strong constraint on the technology for the production of recognition areas in terms of positioning on the substrate provided with its optical format. A positioning defect equal to or greater than the half-pitch of the read tracks along the axis perpendicular to the axis used for tracking of tracks in the optical format, necessarily requires a corrective action that may make it necessary to scrap such a biochip.

Furthermore, the system for slaving the position of the optical head is complex both mechanically and electronically. A specific optical format must also be produced, depending on the size and the pitch of the recognition areas.

One final disadvantage of this method is the limitation of the sampling step, along the direction perpendicular to the tracks, at the track jump.

SUMMARY OF THE INVENTION

This invention overcomes these problems and in particular any positioning defect between the optical format and the recognition areas.

Rather than continuously slaving the optical read head due to information supplied by optical format marks as divulged in document FR-A-2 784 189, in this invention the optical read head is allowed to pass along its predefined scanning path on the surface of the biochip under the control of its associated system and simultaneously record fluorescence information and positioning information derived from the optical format. No slaving or correction of the position of the optical head is done in the plane of the biochip. However, once the fluorescence has been completely or partially recorded, each measurement is repositioned by computer on a fictitious biochip using the position information recorded using the optical format during the fluorescence measurement. Any scanning linearity or scanning regularity defect is then compensated to determine the genuine spatial origin of the recorded fluorescence information (on the biochip).

The solution proposed by the invention simplifies the mechanical and electronic system because it eliminates all slaving of the position of the optical part of the reader.

A first purpose of this invention consists of a biochip comprising a plurality of useful molecular recognition areas distributed with a determined layout to create a format of molecular recognition areas and means for making optical position marks of each molecular recognition area, distributed with a determined layout to form an optical format, wherein the optical format and the format of recognition areas are formats produced independently of each other, means for determining the relative position of the two formats being provided on the biochip. Thus, the optical format and molecular recognition areas may be spatially independent. In particular, they are not necessarily aligned with respect to each other.

Advantageously, the means for determining the relative position of the two formats are molecular recognition areas intended to receive specific biological targets to obtain fluorescent patterns, these molecular recognition areas designed to receive specific biological targets being arranged at locations that are perfectly well located with respect to useful molecular recognition areas.

Preferably, the optical marking means consists of a sequence of areas engraved and non-engraved in the substrate or in a surface layer of the substrate for a composite substrate. These engraved and non-engraved areas may form a checker board. The areas of the checker board may be oblique with respect to the molecular recognition areas.

Preferably, the surface area of each recognition area is greater than the surface area of an engraved area or a non-engraved area of the optical format. For example, it may correspond to several times the surface area of an engraved area.

Molecular recognition areas may be arranged on the optical format. A layer or a stack of thin layers, facilitating reflection of an optical format tracking beam, may be arranged between the optical format and the molecular recognition areas. This layer also participates in slaving of the position of the optical head in the direction perpendicular to the plane of the substrate.

A second purpose of this invention consists of a device for reading a biochip like that defined above, comprising:

a first optical head capable of projecting first incident light onto the biochip, first means for scanning the biochip by the first incident light, a second optical head capable of projecting second incident light on the biochip, second means for scanning the biochip by the second incident light, a first optical system associated with an optical head to project first light originating from the biochip and related to the first incident light onto a first optoelectronic sensor, demonstrating the presence or absence of target molecules on each molecular recognition area, the first optoelectronic sensor being capable of supplying signals corresponding to the first light, a second optical system associated with an optical head to project second light originating from the optical format of the biochip and related to the second incident light onto a second optoelectronic sensor, the second optoelectronic sensor being capable of supplying signals corresponding to the second light, first means for recording at least part of the signals corresponding to the first light, second means for recording at least part of the signals corresponding to the second light, means for processing said signals to adjust the signals corresponding to the first light and signals corresponding to the second light, on a fictitious biochip as a function of means of determining the relative position of the two formats.

Advantageously, the first and second optical heads may be coincident. The processing means may for example be computer means processing said signals as they are acquired or after complete acquisition over the entire biochip.

The read device may comprise a mechanical system or an autofocus system to maintain the focus of the read beam on the surface of the biochip. This autofocus system may include a piezoelectric actuator and means of slaving this actuator.

BRIEF DESCRIPTION OF THE FIGURES

The invention will be better understood and other advantages and special features will become clearer after reading the following description given as a non-limitative example with reference to the appended figures, wherein.

DETAILED PRESENTATION OF PARTICULAR EMBODIMENTS

Figure 1:
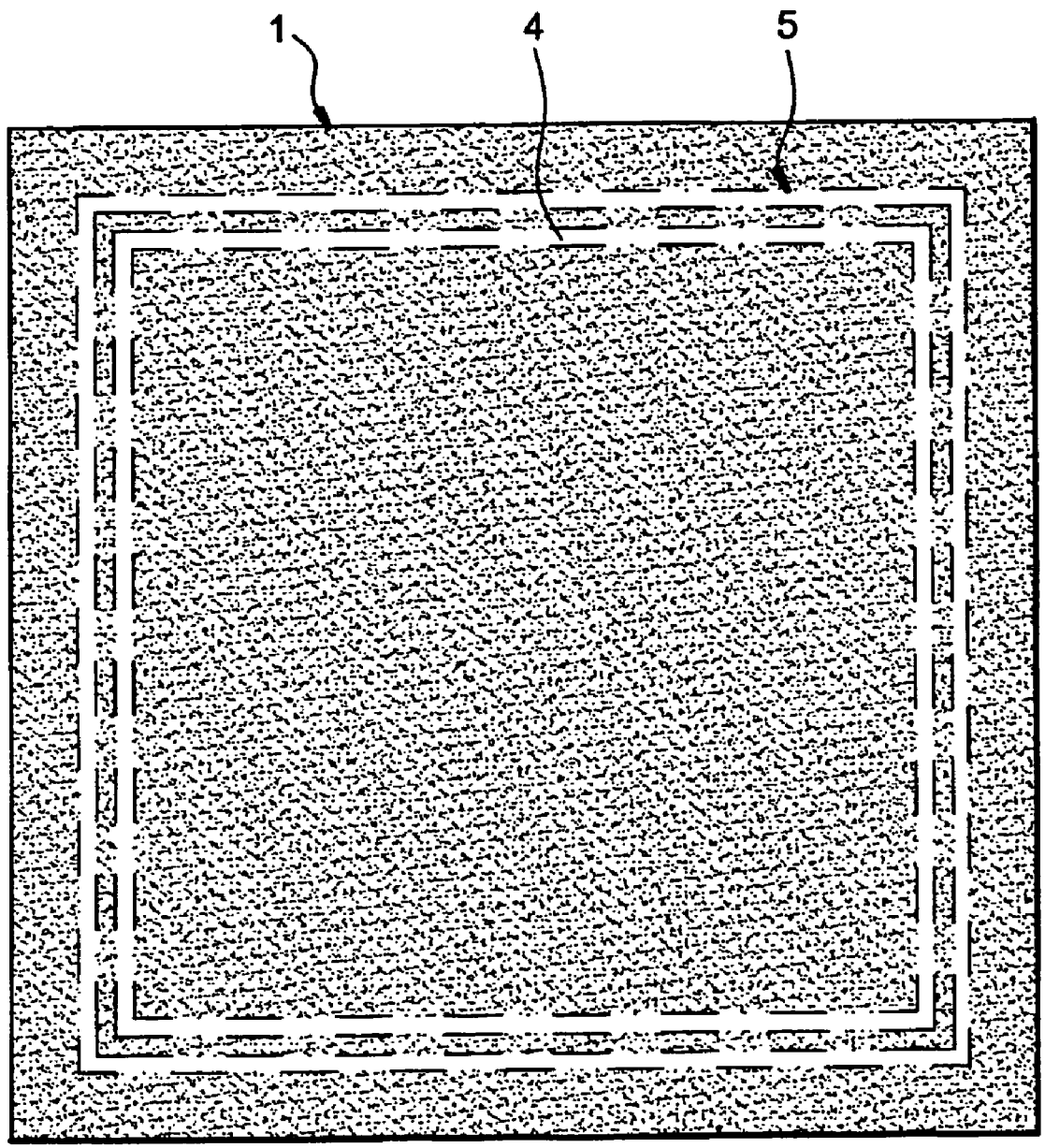
FIG. 1 shows a top view of a biochip according to this invention.

FIG. 1 is a top view of a biochip according to this invention. The biochip may for example be made on a silica wafer 1 transparent to the reading beam. The grey parts show parts comprising the optical format. Many optical formats can be used by this invention. The optical format described here is simply one advantageous embodiment. The optical format will be described with reference to FIG. 2 that is an enlarged view of part of FIG. 1. The biochip may also be made on glass or on transparent plastic, reading being done through the plate. It may also be done on a non-transparent substrate, reading then being done from above, in other words without passing through the substrate.

Figure 2:
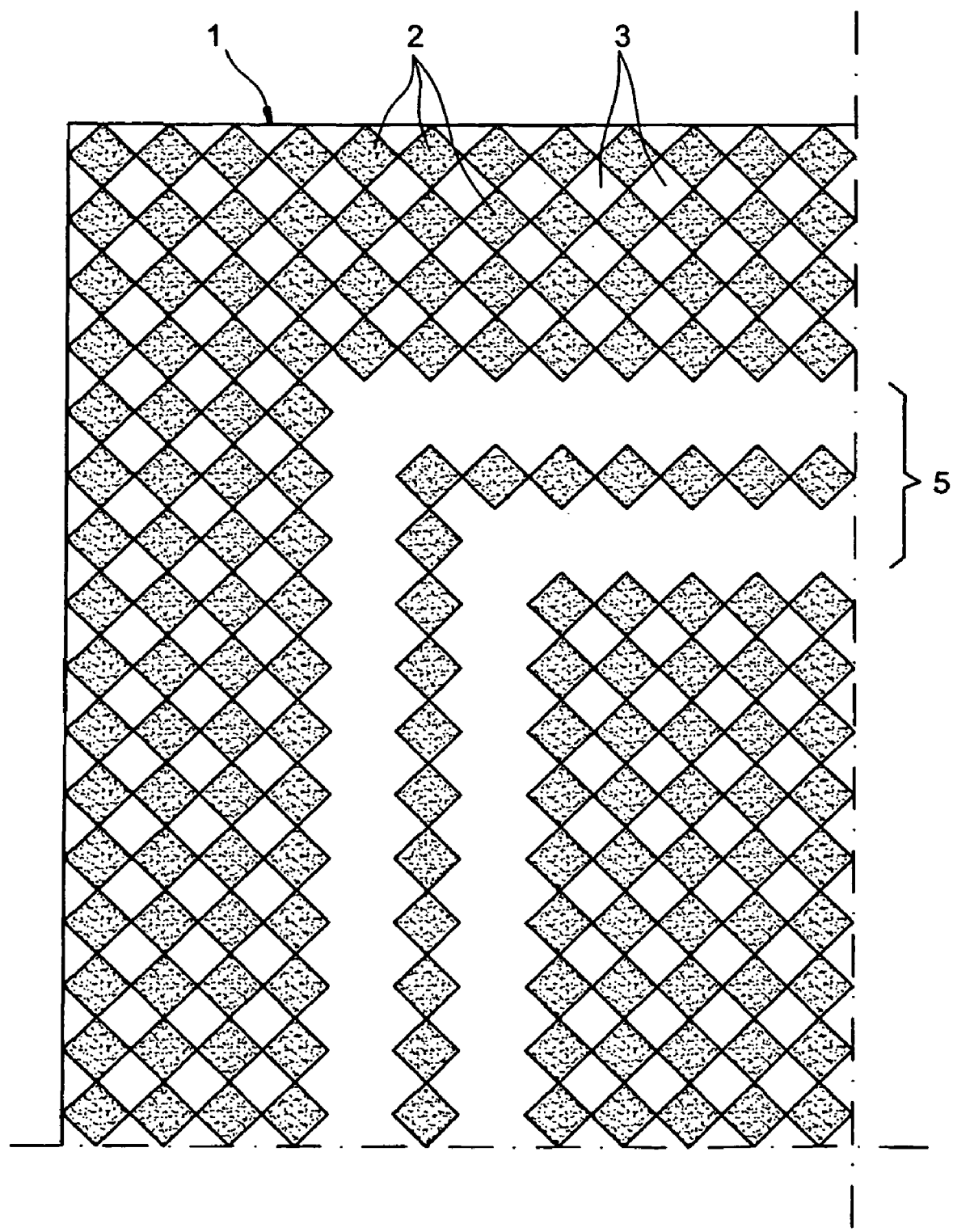
FIG. 2 shows an enlarged view of part of the biochip shown in FIG. 1 showing components of the optical format.

As shown more clearly in FIG. 2, the optical format may consist of a matrix of engraved areas 2 and non-engraved areas 3, for example in the shape of a diamond or a square. Each diagonal of an engraved or non-engraved area may be 5 µm long.

The optical format may comprise a break 5 so as to give a coarse delimitation indication of the part in which the biological recognition areas are made and thus, when scanning is linear, to provide a starting point for the measurements. The area delimited by the break area must be sufficiently large to encompass biological recognition areas regardless of the positioning inaccuracy of the technique for producing the biological recognition areas. The surface area of an engraved area or a non-engraved area corresponds approximately to the surface area of the reading beam spot.

For a substrate made of silica, silicon or glass, engraving may be done using an RIE engraving technique well known in the micro-technologies field. Depending on the design of the optics used in the reader, this engraving may be modified within a range varying from 20 nm to several hundred nanometres. For a substrate made of plastic, moulding or hot stamping techniques may be used.

Figure 3:
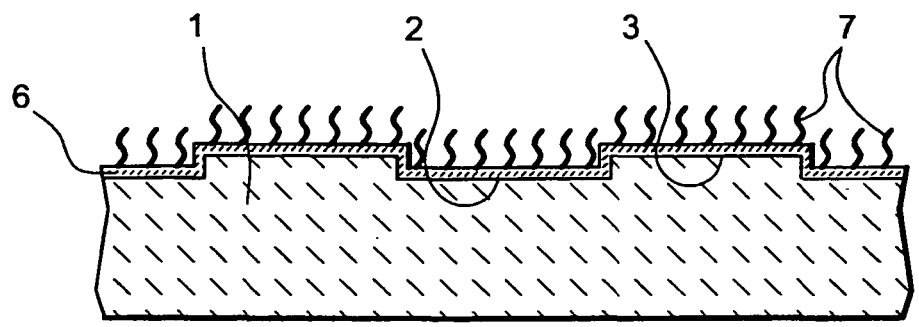
FIG. 3 shows a partial and cross sectional view of a biochip according to the invention showing components of the optical format.

FIG. 3 shows a partial cross-sectional view of the biochip in FIGS. 1 and 2. It shows engraved areas 2 and non-engraved areas 3. The section was made along an axis corresponding to diagonals of successive engraved areas and non-engraved areas.

To optimise operation of optical format position detections, an optical layer 6 or a stack of optical layers is deposited on the engraved face or more generally on the textured face of the plate, in order to achieve reflectivity for example of the order of 10% of incident light. The layer 6 may be an 80 nm thick layer of silicon nitride, with a refraction index equal to 2. Other materials with other indexes may be used depending on the required reflectivity, for example $TiO_2$, $Ta_2O_5$, $HfO_2$, $ZnO$, $MgO$, $SiO_2$, $MgF_2$, $YF_3$, $Al_2O_3$, $ZrO_4Ti$, $Y_2O_3$, diamond and oxynitrides. This is a system optimisation as a function of a large number of parameters: fluorescence level to be measured, transmission of the collection optics, laser power, nature of the substrate and the medium in which the biochip is located, etc.

The optical format chosen here has the advantage that it is symmetric about the two axes. This guarantees equivalent positioning precision on the two axes.

Reference 7 in FIG. 3 diagrammatically shows the biomolecules of molecular recognition areas that are fixed to the optical layer 6, these biomolecules not being shown to scale.

Figure 4:
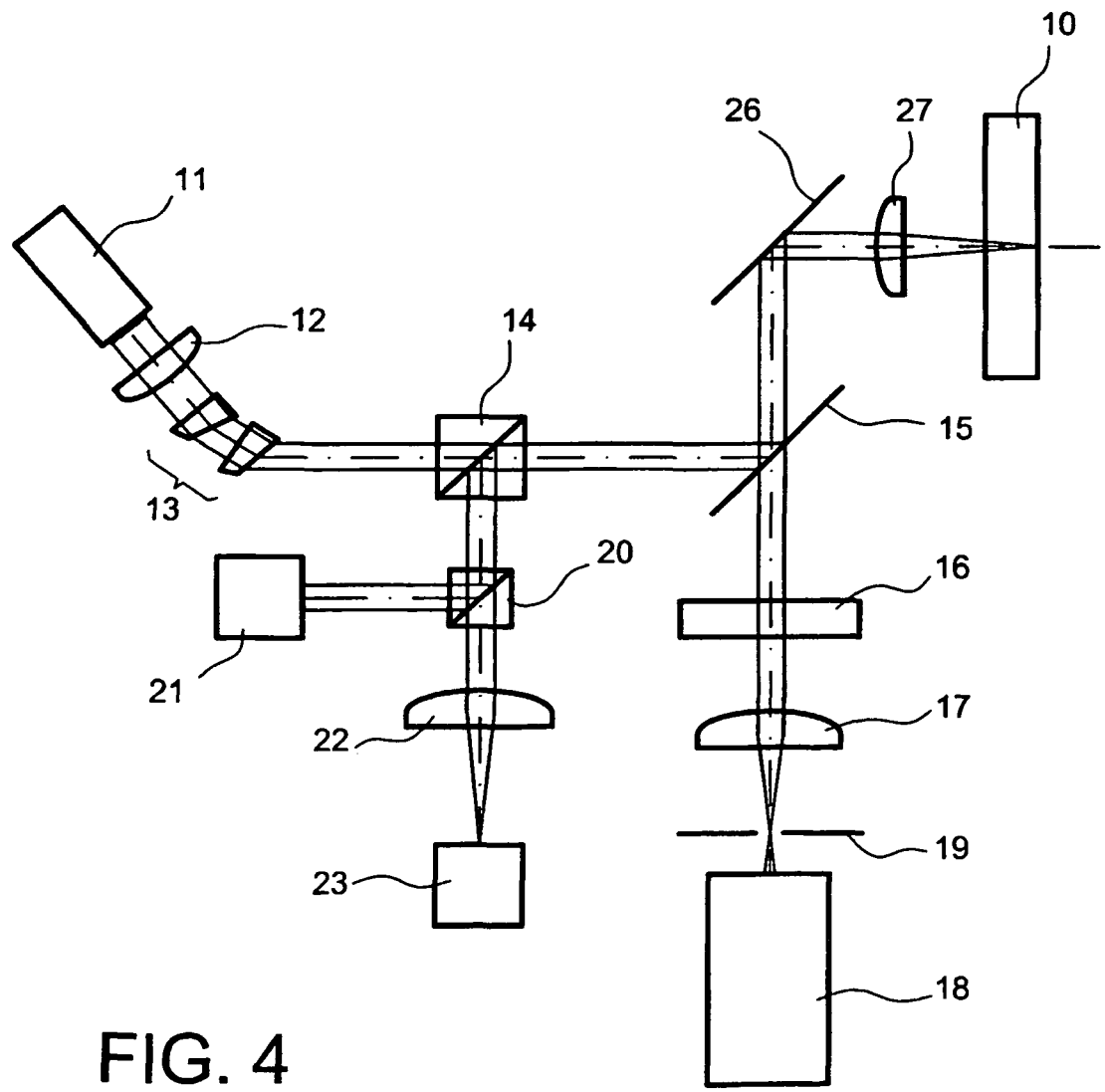
FIG. 4 is a simplified diagram of a reading device according to the invention.

FIG. 4 shows a simplified diagram of a reading device according to the invention.

The device comprises a laser 11 emitting a beam that is processed by a collimation lens 12 and a system 13 of anamorphic prisms and monochromatic filtering.

The processed beam passes through a separating cube 14 to be reflected by the dichroic mirror 15 towards a mirror 26. The mirror 26 reflects the laser beam to the biochip 10 after passing through a focusing lens 27. The excitation beam passes through the biochip 10 and is focussed on the face of the biochip opposite the lens 27.

The focusing lens 27 collects fluorescence light emitted by the biomolecules in response to the excitation light and that is directed towards the mirror 26 to be reflected by this mirror to the optoelectronic sensor 18 after passing through the high pass filter 16, the convergence lens 17 and the confocal diaphragm 19.

The focusing lens 27 also collects excitation light returned by the optical format. This returned light is reflected on the mirror 26, then on the dichroic mirror 15 towards the separating cube 14. It is then returned to a second separating cube 20 that reflects part of this light to the photodiode 21 and the other part to the photodiode 23 after passing through the focusing lens 22.

Information provided by the photodiode 21 contains data about the optical format that will be treated jointly with the fluorescence signal.

Information provided by the photodiode 23 is used for slaving of the position of the focusing lens 27 on the optical axis, since an autofocus system has to be kept, in the same way as for traditional CD readers. This system is conventionally based on slaving of an actuator with electromagnetic control. An additional problem arises for scanning of the biochip by forward-return movement. It is possible that the displacement direction reversal phases occur in areas in which there is no available reflection signal (for example not on the biochip). This is essential in a traditional slaving system and a focus search phase would be necessary at the beginning of the line at every line change. To avoid this loss of time, the proposed autofocus system is capable of holding the actuator in position at the end of each line to resume reading in the reverse direction at the same focusing position obtained for the end of the previous line. For example, one solution consists of using a piezoelectric actuator for holding the position at the end of the line by holding said value.

In this system, the optical format is illuminated at the same time as the biomolecule fluorophores are excited. The format can be illuminated and the fluorophores can be excited using different or identical light sources. A record of the two types of information is then made during this scanning. The fluorescence measurement information is recorded at the same time as information output from the optical format.

The two records result in the creation of two computer files and computer processing is then done and is followed by all operations leading to information being read from the biochips. In particular, the processing may make use of convolution methods. This processing may be done once the biochip has been fully read. It may also occur while acquisitions are taking place during scanning, which among other advantages, reduces the amount of information to be stored.

With the biochips used, relative positions of molecular recognition areas with respect to the optical format is known. Some specific targets were introduced during hybridising of marked biological targets. These specific targets enable the production of fluorescent patterns at specific and predefined locations on the biochip, for example at the four corners of the part located inside the area 5 (see FIG. 1). These fluorescent patterns are used as marks and provide a means of knowing the relative position of the optical format with respect to the positions of the molecular recognition areas. The specific locations may be 4 area by 4 area matrices, each area having a side dimension of 30 µm and one area out of two being provided with biological probes capable of receiving specific targets (specific recognition areas). Obviously, the size of the patterns may be larger or smaller. These specific recognition areas may be arranged at random or not at random in the pattern. They may also have different intensities.

The positions of recognition areas are dependably determined by their manufacturing technique, for example using photolithography masks. Thus, the relative position of the format of recognition areas and the optical format are known. Each fluorescence measurement is correlated to position information, therefore computer processing can be used to reposition this measurement with respect to the real positions of the recognition areas.

This system does not require perfect positioning of recognition areas on the biochip with respect to the patterns forming the optical format. Nor does it necessarily impose regular and uniform reading of each molecular recognition zone. Thus, a large number of readings for each recognition area can be used to make a measurement of the fluorescence value of a biological probe that is just as reliable as a regular and uniform reading.

Figure 5:
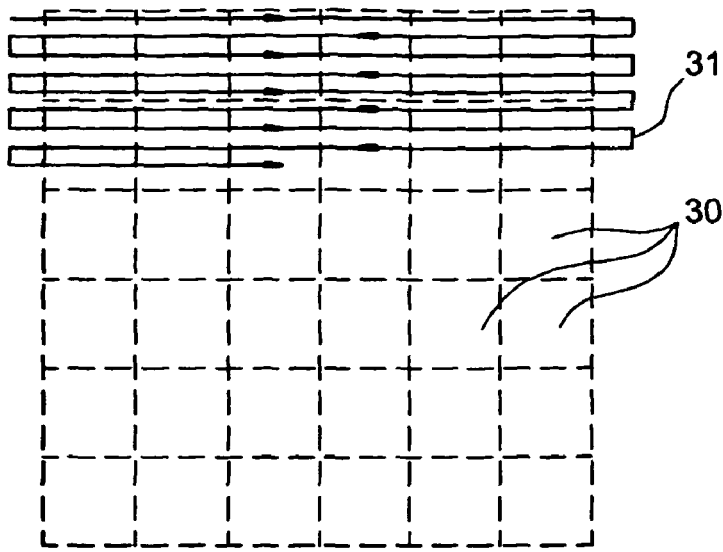
FIG. 5 shows a diagram of a first example of a reading beam scanning recognition areas.

FIG. 5 shows a diagram of a first scanning example of the read beam on recognition areas. The diagram in FIG. 5 shows a matrix of 6×6 molecular recognition areas 30. The reference 31 represents scanning of the reading beam on the biochip. The dimensions of each molecular recognition area may for example be 30 µm×30 µm. Scanning is done in forward and return lines.

Figure 6:
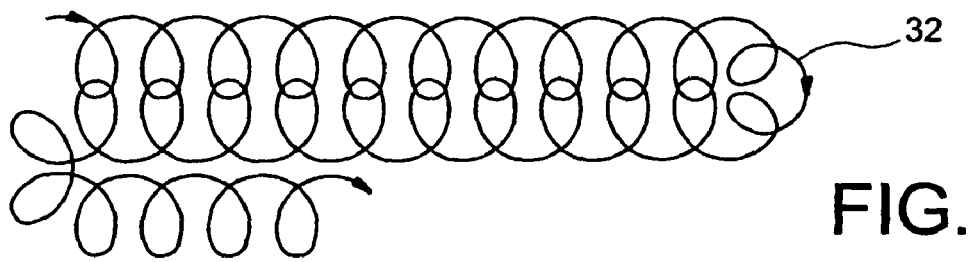
FIG. 6 shows a diagram of a second example of a reading beam scanning recognition areas.

Other scanning methods may be used to give better coverage of the entire surface or to give better agreement with a reliable mechanical system. The forward-return method introduces the problem of deceleration and direction changes in the mechanics. FIG. 6 shows a second possible scanning example. Scanning 32 is done spirally which prevents the need for deceleration.

Figure 7:
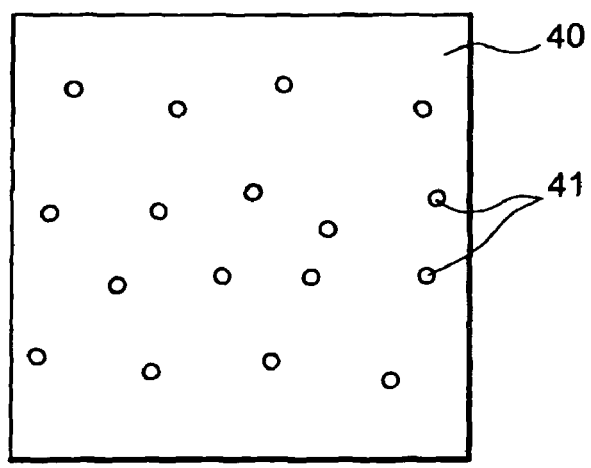
FIG. 7 shows a possible distribution of reading points obtained on a recognition area using this invention.

FIG. 7 shows a possible distribution of reading points 41 obtained on a molecular recognition area 40 using this invention.

The invention claimed is:

1. A biochip comprising:
   a plurality of molecular recognition areas distributed with a determined layout to create a format of molecular recognition areas, wherein the molecular recognition areas include specific recognition areas that have fluorescent patterns, said specific recognition areas being arranged atpredefined locations on the biochip with respect to other areas of the molecular recognition areas; and
   a plurality of optical position marks for the plurality of molecular recognition areas, distributed with a determined layout to form an optical format, wherein the molecular recognition areas and the optical format are spatially independent, and
   the specific molecular recognition areas provide means for determining a relative position of the optical format to the molecular recognition areas.

2. A biochip according to claim 1, wherein the optical position marks includes a sequence of engraved areas and non-engraved areas.

3. A biochip according to claim 2, wherein the engraved areas and non-engraved areas form a checker board.

4. A biochip according to claim 3, wherein areas of the checker board are oblique with respect to the molecular recognition areas.

5. A biochip according to claim 2, wherein a surface area of each recognition area is greater than a surface area of an engraved area or a non-engraved area of the optical format.

6. A biochip according to claim 1, further comprising a layer or a stack of thin layers, facilitating reflection of an optical format tracking beam, arranged between the optical format and the molecular recognition areas.

7. A device for reading a biochip defined in claim 1, comprising:
- a first optical head configured to project first incident light onto the biochip;
- first means for scanning the biochip by the first incident light;
- a second optical head configured to project second incident light onto the biochip;
- second means for scanning the biochip by the second incident light;
- a first optical system associated with an optical head to project first light originating from the biochip and related to the first incident light onto a first optoelectronic sensor, demonstrating presence or absence of target molecules on each molecular recognition area, the first optoelectronic sensor configured to supply signals corresponding to the first light;
- a second optical system associated with an optical head to project second light originating from the optical format of the biochip and related to the second incident light onto a second optoelectronic sensor, the second optoelectronic sensor configured to supply signals corresponding to the second light;
- first means for recording at least part of the signals corresponding to the first light;
- second means for recording at least part of the signals corresponding to the second light; and
- means for processing said signals corresponding to the first light and signals corresponding to the second light on a fictitious biochip and determining a relative position between the optical format and the molecular recognition areas.

8. A device according to claim 7, wherein the optical heads are coincident.

9. A device according to claim 7, further comprising a mechanical system or an autofocus system to maintain focus of a reading beam on a surface of the biochip.

10. A device according to claim 9, wherein the autofocus system includes a piezoelectric actuator and means for slaving the actuator.

11. A biochip according to claim 1, further comprising a break that provides a coarse delimitation indication of where the molecular recognition areas are on the biochip.

12. A biochip according to claim 1, wherein the first areas of the molecular recognition areas are randomly arranged on the optical format.

13. A device according to claim 8, wherein the coincident optical heads are not continuously slaved due to information supplied by the optical position marks, the optical read passes along a predefined scanning path on a surface of the biochip, and fluorescence information and positioning information derived from the optical position marks is simultaneously recorded.

14. A biochip according to claim 1, wherein the optical format and the molecular recognition areas are not aligned with respect to each other.

15. A biochip comprising:
- a plurality of molecular recognition areas distributed with a determined layout to create a format of molecular recognition areas,
- a plurality of optical position marks for the plurality of molecular recognition areas, distributed with a determined layout to form an optical format,
- wherein the optical format and the molecular recognition areas are spatially independent with respect to each other, and
- the biochip provides means for determining a relative position of the optical format and the molecular recognition areas.

16. A biochip according to claim 15, wherein the optical format and the molecular recognition areas are not aligned with respect to each other.

* * * * *